United States Patent [19]

Fex et al.

[11] Patent Number: 5,734,071
[45] Date of Patent: Mar. 31, 1998

[54] PROCESS FOR SEPARATING LIPOPHILIC COMPOUNDS

[75] Inventors: Tomas Fex; Gunnar Olsson, both of Lund, Sweden

[73] Assignee: Trikonex AB, Lund, Sweden

[21] Appl. No.: 628,703

[22] PCT Filed: Oct. 19, 1994

[86] PCT No.: PCT/SE94/00982

§ 371 Date: Apr. 16, 1996

§ 102(e) Date: Apr. 16, 1996

[87] PCT Pub. No.: WO95/11216

PCT Pub. Date: Apr. 27, 1995

[30] Foreign Application Priority Data

Oct. 20, 1993 [SE] Sweden ................................. 9303446

[51] Int. Cl.⁶ ............................................................. C11B 3/00
[52] U.S. Cl. ............................................. 554/186; 426/417
[58] Field of Search ............................... 554/186; 426/417

[56] References Cited

U.S. PATENT DOCUMENTS 5,106,542  4/1992  Traitler et al. ............................ 554/186

FOREIGN PATENT DOCUMENTS 0347509  12/1989  European Pat. Off. .
2180996  7/1990  Japan .
8703899  7/1987  WIPO .

*Primary Examiner*—Gary Geist
*Assistant Examiner*—Deborah D. Carr

*Attorney, Agent, or Firm*—Beveridge, DeGrandi, Weilacher & Young, LLP

[57] ABSTRACT

A process for separating lipophilic compounds from other lipophilic compounds and a kit therefore are described, said process comprises the steps of:

a) providing a mixture of the lipophilic compounds;

b) providing urea dissolved in an inert solvent or solvent mixture in which said lipophilic compounds are at most only slightly soluble;

c) contacting the mixture of lipophilic compounds with the urea, whereby said urea complex forming lipophilic compounds form complexes with the urea, d) separating the whole mixture into a two-phase mixture with lipophilic compounds forming a first phase and the solvent or solvent mixture forming a second phase, where the complexes formed are present as solids in the second phase, and the lipophilic compounds, which have not been complexed with urea, are present in the first phase, e) separating, and optionally purifying, the first phase from the second phase;

f) heating the second phase to break the complexes and release the lipophilic compounds, thereby forming a two-phase mixture, in which the released lipophilic compounds are present in the upper phase, which is removed and optionally purified, and the urea and the solvent or solvent mixture are present in the lower phase, and, optionally, g) adding a new mixture of lipophilic compounds to be separated to the urea in the solvent or solvent mixture, and repeating steps a)–g) above one or more times.

23 Claims, No Drawings

1

PROCESS FOR SEPARATING LIPOPHILIC COMPOUNDS

This application is a 371 of PCT/SE94/00982 filed Oct. 19, 1994.

BACKGROUND OF THE INVENTION

The present invention relates to a process for separating lipophilic compounds from other lipophilic compounds.

Urea (carbamide) and lipophilic compounds, e.g. fatty acids (or derivatives thereof, such as their lower alkyl esters) can under certain conditions form solid urea inclusion complexes (for a review see: D. Swern, "Urea Complexes in Fatty Acids", part III, ed. K.S. Markley, Interscience Publishers 1964). The stability of the complexes are highly dependent on the degree of unsaturation in the fatty acids, saturated fatty acids forming the most stable and polyunsaturated fatty acids forming the least stable complexes. In addition, stability increases with increasing chain length and is reduced by substituents on the fatty acid chain.

Urea crystallisation methodology has for example been used to prepare a concentrate of fish oil ethyl esters enriched in valuable n–3 polyunsaturated fatty acids.

The crystallisation procedure is typically performed by dissolving a mixture of fatty acids (or their derivatives) in a hot alcohol solution containing the appropriate amount of urea. The solution is cooled, whereby solid urea complexes are formed. These are removed by filtration, and after evaporation of the solvents from the mother liquor a fraction enriched in e.g. unsaturated fatty acids is obtained. When urea crystallisation is performed according to this procedure it requires filtration of large amounts of urea complexes and also evaporation of large amounts of solvents to isolate the non-complexing fatty acids. In addition, no simple method has been devised to regenerate the urea.

Japanese patent application JO 2180996-A describes a multistep procedure which allows for regeneration of urea. As mentioned above, crystallisation takes place under conditions where the fatty acids (or their derivatives) are totally dissolved in methanol, but utilises a solvent extraction to isolate the non-complexing fatty acid derivatives (and the fatty, acid derivatives liberated from the complexes by heating). Subsequently, the solvents need to be evaporated. The use of an extraction solvent limits the potential applications, since the components to be fractionated may be difficult to extract.

DESCRIPTION OF THE INVENTION

The object of the present invention is to eliminate the above-mentioned disadvantages in the state of art, and to provide an efficient and economical process for separating lipophilic compounds from other lipophilic compounds by use of a urea crystallisation procedure for purification of lipophilic compounds, e.g. fatty acids and fatty acid derivatives, which allows for continuous regeneration of urea and simple procedures for product isolation, not requiring solvent extraction.

This object of the present invention is achieved by a process as initiallly described, further characterised by a) providing a mixture of the lipophilic compounds;

b) providing urea dissolved in an inert solvent or solvent mixture in which said lipophilic compounds are at most only slightly soluble;

c) contacting the mixture of lipophilic compounds with the urea, whereby said urea complex forming lipophilic compounds form complexes with the urea, d) separating the whole mixture into a two-phase mixture with lipophilic compounds forming a first phase and the solvent or solvent mixture forming a second phase, where the complexes formed are present as solids in the second phase, and the lipophilic compounds, which have not been complexed with urea, are present in the first phase, e) separating, and optionally purifying, the first phase from the second phase;

f) heating the second phase to break the complexes and release the lipophilic compounds, thereby forming a two-phase mixture, in which the released lipophilic compounds are present in the upper phase, which is removed and optionally purified, and the urea and the solvent or solvent mixture are present in the lower phase, and, optionally, g) adding a new mixture of lipophilic compounds to be separated to the urea in the solvent or solvent mixture, and repeating steps a)–g) above one or more times.

Further embodiments of the present invention are given in the subsequent claims.

According to the present invention, it has been found that the urea crystallisation procedure can be performed under heterogeneous conditions using a solvent or solvent mixture, wherein the lipophilic compounds, e.g. fatty acids or derivatives thereof, are at most only slightly soluble. This has been developed into advantages, allowing for both continuous regeneration of urea and simple procedures for isolation of the products.

In the process according to the present invention, urea is first dissolved in a solvent or solvent mixture. Preferably the solvent or solvent mixture is hot. The mixture of lipophilic compounds is added and a two-phase mixture results with the lipophilic compounds in the upper phase and the dissolved urea in the lower phase. This two-phase mixture is stirred thoroughly while cooling. When the formation of the urea complexes has been completed the complexes are present as solids in the bottom of the lower phase of the newly formed two-phase mixture. The non-complexing lipophilic compounds are present in the upper phase and are separated from the mixture and, optionally, purified. Subsequently, the remaining mixture containing the complexes and the solvent or solvent mixture is heated to dissolve the urea complexes, whereby the released lipophilic compounds are concentrated in the upper phase of the newly formed two-phase mixture and are separated and optionally purified. Thereafter, if desired or required, a new portion of starting material, i.e. a mixture of lipophilic compounds, is added and the procedure is repeated. This can be done several times to provide an almost continuous process. Small amounts of urea solution may accompany the separated lipophilic compounds and are easily removed from these, e.g. by washing with a water solution. The amount of urea solution lost in this way may be replenished.

As mentioned above, the solvents or solvent mixtures to be used in the process according to the present invention are characterised by the fact that the lipophilic compounds are only slightly soluble therein. The expression "slightly soluble" as used herein means that the solubility of the lipophilic compounds in the solvent or solvent mixture is generally less than 10% (vol%/vol%) and preferably less than 5% (vol%/vol%). Thus, the complex formation is performed under heterogeneous conditions in a two-phase mixture. As to separation of lipophilic compounds using a urea crystallisation procedure, this has never been done before in the prior art under heterogeneous conditions.

The choice of solvent or solvent mixture then, of course, depends on the exact properties of the lipophilic compounds that are to be separated. In most cases a mixture of organic solvent(s) and water can be used. The organic solvent may be a lower alcohol such as methanol, ethanol, isopropanol, n-propanol and the like. Polyhydric alcohols such as ethanediol, 1,2-propanediol, 1,2-propanediol, glycerol and the like may also be used. Other solvents which may be used include e.g. dimethylformamide, dimethylsulfoxide and acetonitrile. All of the organic solvents mentioned above can be used individually in the process according to the invention, except from methanol, which is used only in a solution of water. In a preferred embodiment a solution of 70–95%, preferably 75–90%, methanol in water or 60–80%, preferably 65–80%, ethanol in water is used as solvent. For example, when fish oil ethyl esters are to be separated, a suitable solvent mixture may consist of water containing between 65 and 80% of ethanol. Mixtures of two or more of the solvents mentioned above may also be used.

The amount of solvent or solvent mixture may vary according to the type of separation and is typically 3–10 times, based on the volume, the amount of the lipophilic compounds in the starting material.

The amount of urea may also vary according to the type of separation and is typically 3–5 times by weight of the amount of lipophilic compounds in the starting material which are to be complexed.

The crystallisation procedure is suitably performed by using initial temperatures ranging from boiling point to room temperature, and using final temperatures ranging from +40° C to −20° C. In particular instances, when the compounds to be separate form urea complexes of low stability, even lower temperatures may be used.

Various additives such as inorganic salts (e.g. sodium chloride, sodium sulphate) may be added to improve e.g. phase separations. Additives, such as inorganic acids, for example HCl and $H_2SO_4$ may also be added for this purpose. Addition of various lipophilic solvents may also be of interest in this context.

To avoid oxidation the process may be performed under an atmosphere of inert gas, such as nitrogen, and/or antioxidants may be added. Complexing agents such as ethylenediaminetetraacetic acid (EDTA) and derivatives thereof can be used to complex metal ions which may otherwise participate in oxidative reactions.

The process according to the present invention can be performed in several steps, especially if an improved fractionation is desired.

In one embodiment of the process according to the present invention, the urea solution is recycled into the process together with the solvent or solvent mixture.

The process according to the present invention is applicable to all separations where a mixture of lipophilic compounds can form complexes with urea and where the complexes of the various compounds have different stabilities. All such separations are also within the scope of the present invention. The expression "lipophilic compounds" as used herein, refers mainly to fatty acids and derivatives thereof, but also includes fatty alcohols and alkanes. Further, gamma-linolenic acid and/or its derivatives can be purified from oils where it is present. Eicosapentaenoic acid (EPA) and docosahexenoic acid (DHA) and/or their derivatives can be separated from each other, taking advantage of the different stabilities of their urea complexes. Branched fatty acids and/or their derivatives can be purified from products where they are present. 1-monoglycerides, 2-glycerides, 1,2-diglycerides and 1,3-diglycerides may form urea complexes of different stabilities. Further, saturated alkanes can be separated from unsaturated alkanes, and straight chain alkanes from branched alkanes.

The process of the present invention yields in many instances products of sufficient purity which can be used as such. In other instances, when further purification is desirable, the process of the present invention provides a primary enrichment which will improve capacity and separation properties of a second step. A preferred embodiment of the inventive process involves the preparation of a fish oil ester concentrate containing high amounts of EPA and DHA which may be further purified by e.g. chromatographic techniques to increase concentrations further, and also to yield e.g pure EPA and DHA, respectively.

Concentrates of EPA and DHA as obtained by the present invention are of interest for various medical applications due to the beneficial effects of these fatty acids. (See e.g. L. E. Kinsella "Seafoods and Fish Oils in Human Health and Desease", Marcel Decker, 1987.)

The invention also includes a kit for separating lipophilic compounds from other lipophilic compounds, comprising a solvent or solvent mixture, urea, inorganic salts, inorganic acids and optionally complexing agents.

It is to be understood that, while the invention has been described in conjunction with the preferred embodiment thereof, the foregoing description as well as examples which follow are intended to illustrate and not to limit the scope of the invention. Other aspects, advantages and modifications within the scope of the invention will be apparent to those skilled in the art to which the invention pertains.

EXAMPLE 1

300 ml of ethanol/water (75:25, v/v), 175 g of urea, 1 g of sodium sulphate and 0.4 g of EDTA (Na-salt) were heated to about 70° C to dissolve the urea. Then 50 g of fish oil ethyl esters was added, containing 18% EPA and 12% DHA. The mixture was stirred thoroughly and allowed to cool slowly to room temperature. The solid precipitate was allowed to settle at the bottom, and from the top about 15 g of an oil was collected from which ethyl esters containing about 70% EPA+DHA could be isolated. The remainder was heated to about 70° C to dissolve the urea complexes.

About 35 g of oil was collected, and from this ethyl esters containing only 15% EPA+DHA were isolated.

An additional 50 g of esters was added to the remaining urea solution, and the process was repeated to yield products of similar characteristics as those mentioned above.

In a similar experiment, 5 g of NaCl was used instead of sodium sulphate, and 1 g of BHA (butylated hydroxyanisole) was added to minimise oxidation.

Yet another experiment was carried out under an atmosphere of nitrogen, also to minimise oxidation.

EXAMPLE 2

1500 ml ethanol/water (75:25, v/v), 875 g of urea, 5 g of sodium sulphate and 2.5 g of EDTA (Na-salt) were heated to about 70° C to dissolve the urea. Then 380 g of fish oil ethyl esters .containing about 15% EPA+DHA was added. The mixture was stirred thoroughly and allowed to cool at 15° C. 66 g of non-complexing esters (containing about 50% EPA+DHA) separated and were cooled. The remainder was heated to about 70° C to dissolve the urea complexes, and the oil which separated was removed.

To the urea mixture was now added 250 g of a fish oil ethyl ester concentrate (containing about 50% EPA+DHA), using the same crystallisation procedures. as above. 88 g of the product (containing about 79% EPA+DHA) was isolated.

EXAMPLE 3

440 ml of methanol/water (80:20, v/v), 260 g of urea and 0.5 g of sodium sulphate was heated to dissolve the urea. 150 g of a fatty acid mixture containing 67% of linoleic acid was added. The mixture was stirred thoroughly and cooled to about 10° C. The solid precipitate was allowed to settle at the bottom and from the top a fraction was collected from which about 70 g of a product containing 94% linoleic acid was isolated.

EXAMPLE 4

40 g of urea and 0.05 g of sodium sulphate was dissolved in 75 ml of methanol/water (82:18, v/v) by heating. 50 g of oleic acid (about 85% purity) was added and the mixture was stirred thoroughly and cooled to 5–10° C. The mixture was stirred slowly to allow the urea complexes to settle at the bottom, and from the top a fraction was collected, from which oleic acid of about 93% purity could be isolated. The remainder was mainly linoleic acid.

Oleic acid of higher purity was obtained by forming urea complexes of the product above, and removing the non-complex forming acids (mainly linoleic acid). Heating the complex liberated the complexing acids and could give oleic acid of very high purity.

EXAMPLE 5

500 g of urea, 0.5 g of sodium sulphate and 0.3 g of EDTA (Na-salt) in 850 ml of 75% ethanol were heated to dissolve the urea. 180 g of butter oil ethyl esters (containing about 1% of branched fatty acids) was added, and the mixture was stirred thoroughly and cooled to room temperature. The solid precipitate was allowed to settle, and from the top 20 g of a fraction enriched in branched fatty acid esters was collected. These 20 g were treated similarly with 40 g of urea, 0.1 g of sodium sulphate and 0.1 g EDTA (Na-salt) in 70 ml of 75% ethanol to yield 8 g of a fraction which contained about 10% of branched fatty acid esters.

We claim:

1. A process for separating a urea complex forming lipophilic compound from another lipophilic compound, comprising;
   a) providing a mixture of the lipophilic compounds to be separated;
   b) providing an inert solvent solution of urea in which said lipophilic compounds are at most only slightly soluble;
   c) contacting the mixture of lipophilic compounds with said urea solution, whereby said urea complex forming lipophilic compound forms a complex with the urea,
   d) separating the whole mixture into a two-phase mixture with lipophilic compounds forming a first phase and the inert solvent forming a second phase, where said complex formed is present as solids in the second phase, and the lipophilic compound, which has not been complexed with urea, is present in the first phase,
   e) separating, and optionally purifying, the first phase from the second phase;
   f) heating the second phase to break the complex and release the lipophilic compound, thereby forming a liquid two-phase mixture, in which the released lipophilic compounds is present in the upper phase, which is removed and optionally purified, and the urea and the inert solvent are present in the lower phase, and, optionally,
   g) adding a new mixture of lipophilic compounds to be separated to the urea in the inert solvent, and optionally repeating steps a)–g) above one or more times.

2. A process according to claim 1, wherein the solubility of the lipophilic compounds in the inert solvent is less than 10% (vol%/vol%).

3. A process according to claim 1, wherein the inert solvent is selected from the group consisting of lower alcohols, polyhydric alcohols, dimethylformamide, dimethylsulfoxide, acetonitrile, water, and mixtures thereof in a ratio of 3–10 times by volume, based on the volume of the lipophilic starting compounds.

4. A process according to claim 1, wherein a solution of 70–95 vol%, methanol in water, or a solution of 60–80 vol% ethanol in water is used as the inert solvent.

5. A process according to claim 1, wherein, a fatty acid or derivative thereof is separated.

6. A process according to claim 5, wherein the derivative is selected from the group consisting of a lower alkyl fatty acid ester, an n–3 polyunsaturated fatty acid lower alkyl ester, oleic acid, linoleic acid, and a branched fatty acid.

7. A process according to claim 6, wherein eicosapentaenoic acid (EPA) and docosahexenoic acid (DHA) are separated from a mixture of fish oil ethyl esters.

8. A process according to claim 1, wherein the whole mixture is brought into a two-phase mixture by centrifugation.

9. A process according to claim 3 wherein the polyhydric alcohol is selected from the group consisting of ethanediol, 1,2-propanediol, 1,3-propanediol and glycerol, and the lower alcohol is selected from the group consisting of methanol, ethanol, isopropanol and n-propanol.

10. A process according to claim 1 wherein, an inorganic salt is added to said whole mixture.

11. A process according to claim 10 wherein, said inorganic salt is selected from the group consisting of sodium chloride, sodium sulphate, and mixtures thereof.

12. A process according to claim 1 wherein, an acid is added to said whole mixture.

13. A process according to claim 12 wherein, said acid is selected from the group consisting of hydrochloric acid, sulphuric acid, and mixtures thereof.

14. A process according to claim 1 wherein, an antioxidant is added to the whole mixture.

15. A process according to claim 14 wherein the antioxidant is BHA.

16. A process according to claim 1 including, conducting the separation under an atmosphere of nitrogen.

17. A process according to claim 1 wherein, the compound separated is selected from the group consisting of a 1-monoglyceride, a 2-glyceride, a 1,2-diglyceride, a 1,3-diglyceride and mixtures thereof.

18. A process according to claim 2, wherein the solubility of the lipophilic compounds in the solvent is less than 5% (vol%/vol%).

19. A process according to claim 4, wherein a solution of 70–90 vol%, methanol in water, or a solution of 65–80 vol%, ethanol in water is used as the solvent.

20. Kit for separating lipophilic compounds from other lipophilic compounds, comprising;
   a) an inert solvent according to claim 1,
   b) urea in an amount of 3–5 times, based on weight, the amount of lipophilic compound to be complexed, and, optionally,
   c) inorganic salts, inorganic acids and, optionally,
   d) complexing agents.

21. A process for separating a urea complex forming lipophilic compound from another lipophilic compound, comprising;
   a) providing a mixture of the lipophilic compounds to be separated;

b) providing an inert solvent solution of urea in which said lipophilic compounds are at most only slightly soluble;

c) contacting the mixture of lipophilic compounds with said urea solution, whereby said urea complex forming lipophilic compound forms a complex with the urea, d) separating the whole mixture into a two-phase mixture with lipophilic compounds forming a first phase and the solvent forming a second phase, where said complex formed is present as solids in the second phase, and the lipophilic compound, which has not been complexed with urea, is present in the first phase, e) separating, and optionally purifying, the first phase from the second phase.

22. A process for separating a urea complex forming lipophilic compound from another lipophilic compound, comprising;

a) providing a mixture of the lipophilic compounds to be separated;

b) providing an inert solvent solution of urea in which said lipophilic compounds are at most only slightly soluble;

c) contacting the mixture of lipophilic compounds with said urea solution, whereby said urea complex forming lipophilic compound forms a complex with the urea, d) separating the whole mixture into a three-phase mixture with lipophilic compounds forming a first phase, the solvent forming a second phase, and said complex formed is present as solids as a third phase, and the lipophilic compound, which has not been complexed with urea, is present in the first phase, e) separating, and optionally purifying, the first phase from the second and third phase.

23. A process for separating a urea complex forming lipophilic compound from another lipophilic compound, comprising;

a) providing a mixture of the lipophilic compounds to be separated;

b) providing an inert solvent solution of urea in which said lipophilic compounds are at most only slightly soluble;

c) contacting the mixture of lipophilic compounds with said urea solution, whereby said urea complex forming lipophilic compound forms a complex with the urea, d) separating the whole mixture with lipophilic compounds forming a first phase, the solvent forming a second phase, e) separating, and optionally purifying, the first phase from the second phase.

* * * * *